United States Patent [19]
Mohr et al.

[11] Patent Number: 5,824,318
[45] Date of Patent: Oct. 20, 1998

[54] AVIRULENT HERPETIC VIRUSES USEFUL AS TUMORICIDAL AGENTS AND VACCINES

[75] Inventors: Ian J. Mohr, Fort Lee; Yakov Gluzman, deceased, late of Upper Saddle River, both of N.J., by Ilan Gluzman, administrator

[73] Assignee: American Cyanamid Company, Madison, N.J.

[21] Appl. No.: 686,631

[22] Filed: Jul. 24, 1996

[51] Int. Cl.$^6$ .............................. A61K 39/245; C12N 7/02
[52] U.S. Cl. ..................... 424/229.1; 424/573; 435/239
[58] Field of Search ................................ 424/229.1, 573; 435/239

[56] References Cited

U.S. PATENT DOCUMENTS 5,328,688  7/1994  Roizman .............................. 424/205.1

FOREIGN PATENT DOCUMENTS 0 514 603  11/1992  European Pat. Off. ....... A61K 35/76
WO96/00007  1/1996  WIPO .
WO96/03997  2/1996  WIPO .

OTHER PUBLICATIONS

Chou, J. et al., Proc. Natl. Acad. Sci. USA, vol. 89, pp. 3266–3270 (1992).

Chou, J. et al., Science, vol. 250, pp. 1262–1266 (1990).

Markert J. et al. Neurosurgery, vol. 32, No. 4, pp. 597–603, Apr. 1993.

Chambers, R., et al., Proc. Nat'l. Acad. Sci. USA, 92:1411–1415 (1995).

*Primary Examiner*—Ponnathapura Achutamurthy
*Assistant Examiner*—Phuong T. Bui
*Attorney, Agent, or Firm*—Elizabeth M. Barnhard

[57] ABSTRACT

Isolated tumoricidal herpetic viruses, in particular neurotrophic herpes viruses, T-lymphotrophic viruses, and B-lymphotrophic viruses, which are avirulent and capable of selectively replicating in and destroying neoplastic cells, and pharmaceutical compositions, vaccines, and methods of destroying neoplastic cells employing the isolated tumoricidal herpetic viruses are described. A method of isolating tumoricidal herpetic viruses by sequentially passaging attenuated, avirulent herpetic viruses on neoplastic cells which fail to support replication of the herpetic viruses and isolating the viruses which grow on the neoplastic cells is also described. Herpes simplex virus mutants having a genome from which the $\gamma 34.5$ genes have been deleted and which require at least one additional mutation to produce a non-neurovirulent herpes simplex virus which selectively replicates in and destroys neoplastic cells are also described.

12 Claims, 11 Drawing Sheets

10, 100, or 1000 pfu virus $10^6$ SKNSH cells 48 hrs freeze - titer on Vero

|  | input pfu | yield SKNSH |
|---|---|---|
| Δ 34.5 | 10 | -- |
|  | 100 | 10 |
|  | 1000 | 125 |
| REV 4 | 10 | 40 |
|  | 100 | 1040 |
|  | 1000 | 6400 |
| wt | 10 | 12,000 |
|  | 100 | $5.6 \times 10^5$ |

FIG. 6A

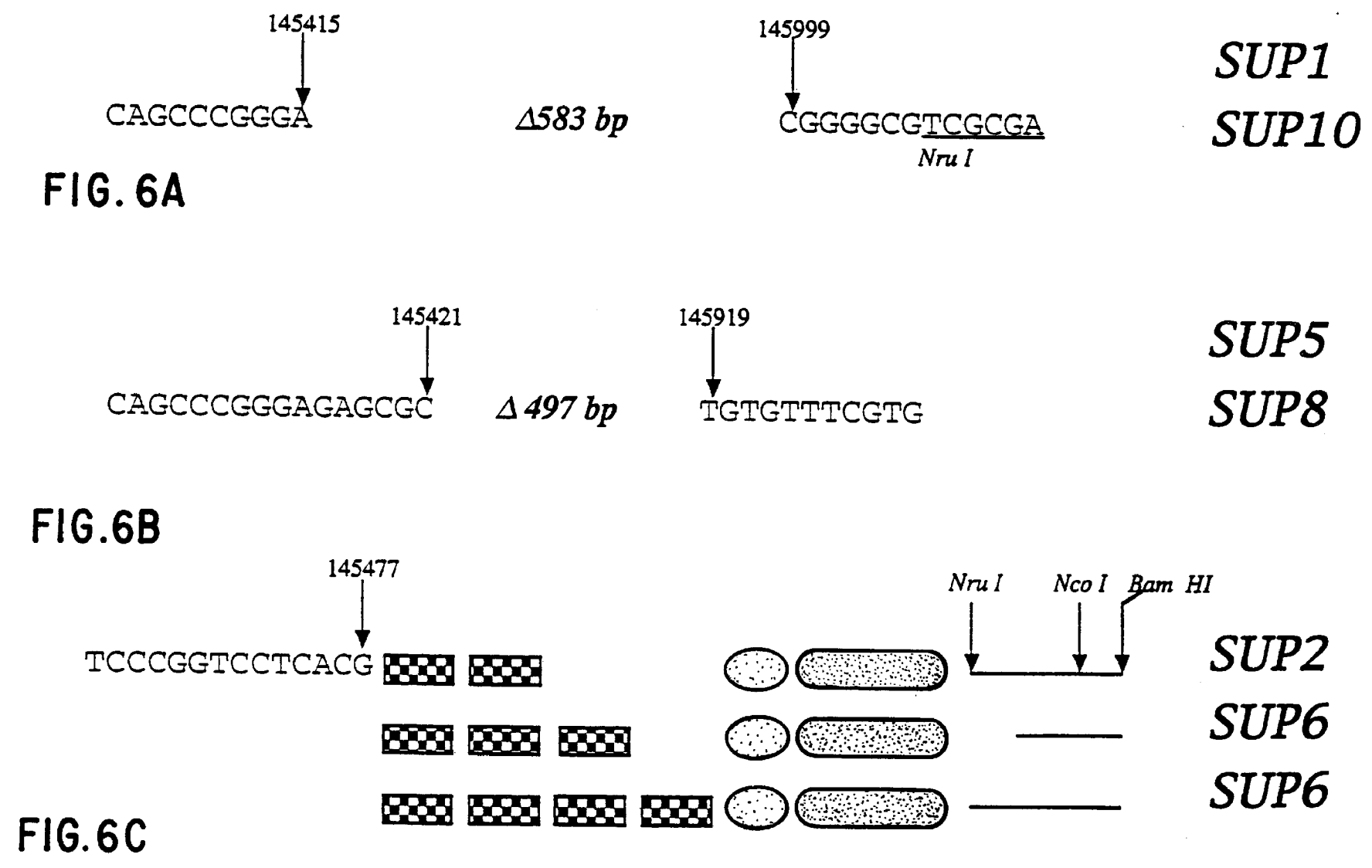

SUP1
SUP10

145415 → CAGCCCGGGA

Δ583 bp

145999 → CGGGGCGTCGCGA
              Nrul

FIG. 6B

SUP5
SUP8

145421 → CAGCCCGGGAGAGCGC

Δ497 bp

145919 → TGTGTTTCGTG

FIG. 6C

SUP2
SUP6
SUP6

145477 → TCCCGGTCCTCACG

Nrul   Ncol  BamHI

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

C A G C C C G G G A           1 0

( 2 ) INFORMATION FOR SEQ ID NO:2:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

C G G G G C G T C G   C G A           1 3

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CAGCCCGGGA GAGCGC 16

(2) INFORMATION FOR SEQ ID NO:4:

(i) SEQUENCE CHARACTERISTICS:
    (A) LENGTH: 11 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:4:

TGTGTTTCGT G 11

(2) INFORMATION FOR SEQ ID NO:5:

(i) SEQUENCE CHARACTERISTICS:
    (A) LENGTH: 14 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:5:

TCCCGGTCCT CACG 14

(2) INFORMATION FOR SEQ ID NO:6:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:6:

CCTCCCGGTC TCACG 15

(2) INFORMATION FOR SEQ ID NO:7:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:7:

CCCTTTTATT GA 12

(2) INFORMATION FOR SEQ ID NO:8:

(i) SEQUENCE CHARACTERISTICS:
    (A) LENGTH: 10 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:8:

TCCCGGTCCT 10

(2) INFORMATION FOR SEQ ID NO:9:

(  i  ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:9:

CCCTCCGCCC AGAGACTCG                                                                               1 9

AVIRULENT HERPETIC VIRUSES USEFUL AS TUMORICIDAL AGENTS AND VACCINES

TECHNICAL FIELD

This invention relates to a method of isolating herpetic viruses, in particular neurotrophic herpes viruses, T-lymphotrophic viruses, and B-lymphotrophic viruses, which are avirulent and capable of replicating in and destroying neoplastic cells, by sequentially passaging attenuated, avirulent herpetic viruses on neoplastic cells which fail to support replication of the avirulent herpetic viruses and isolating the viruses which grow on the neoplastic cells. The invention further relates to pharmaceutical compositions, vaccines, and methods of destroying neoplastic cells employing the isolated herpetic viruses.

BACKGROUND OF THE INVENTION

Viruses are obligate intracellular parasites which have evolved highly complex and specialized relationships with their hosts. While some viruses can establish relatively asymptomatic, persistent infections, others are more virulent and infection results in significant morbidity. Because viruses are specialized assemblies which rely on their host cells for replication and dissemination of progeny, the viruses must therefore ensure that the host they have chosen will survive. It has become increasingly clear that many viruses actually encode functions which may foster the survival of the infected cell. The length of survival time will be quite variable, and responsive to external environmental parameters and the fitness of the host. In the case of more virulent viruses, it is only important to ensure host survival long enough to permit the replication and spread of infectious virus. In the absence of dominant viral survival functions, death programs intrinsic to the host cell become activated and the infectious process is effectively aborted. Development of novel modes of antiviral chemotherapy and the modulation of viral virulence are dependent upon a detailed understanding of this process.

The parameters which govern virulence have long been recognized to be of medical importance. The observation by Jenner in the late 1700's that milkmaids exposed to cowpox failed to contract smallpox led him to examine the use of cowpox virus as a vaccine against smallpox. Unbeknownst to him at the time, the key components responsible for the success of this approach were the high degree of similarity in the overall antigenicity of the two related viruses, and the fact that cowpox was significantly less virulent than its smallpox cousin. The molecular basis for this difference in virulence remains a mystery to this day. Events in more recent history involve the isolation of attenuated viruses which lack the virulence properties of their wild-type counterparts. These live virus preparations can be used as vaccines, as they present a relatively normal display of viral antigens in the context of mild viral infection. Both of these strategies effectively led to the elimination of smallpox and a great decrease in the incidence of polio.

In addition to their use as vaccine strains, there have been reports of tumoricidal effects of viral infections which date back to the turn of the century. These observations suggest that malignant lesions could regress in response to viral infection. The use of viruses as treatments for malignancies, however, must involve the isolation of strains with selective virulence. To be effective in treatments of malignancies, such isolates should only grow productively and exhibit virulence in neoplastic cells, and should not be capable of propagating a productive infection through surrounding normal, terminally differentiated tissue. As virulence is governed by specific viral genes, one approach would be to try to genetically alter the virulence of viruses to obtain viruses which selectively destroy neoplastic cells.

Cancer is a proliferative disease whereby neoplastic cells, which have their derivation from a single malignant cell, grow in an unregulated manner and spread throughout the body. In addition to the surgical removal of isolated tumors, current therapies to treat the various forms of cancer revolve around the enhanced sensitivity of malignant cells to a variety of toxic agents. This reflects the fact that the rapidly dividing, undifferentiated neoplastic cells display a heightened sensitivity to the killing potentiated by radiation and chemicals. Normal, terminally differentiated cells are more resistant to the damage or are, perhaps, more proficient at repairing damage to their DNA. Recent advances in the fields of radiotherapy and chemotherapy have involved attempts to improve on the selective targeting of radioligands or cytotoxic reagents to neoplastic cells.

The current modalities of treatment, surgery, radiotherapy, and chemotherapy, have made little impact on the prognosis of some cancers such as gliomas. Gliomas comprise the most common class of human brain tumors. Non-resectable, aggressively growing brain lesions such as glioblastoma, the glioma that occurs with greatest frequency, prove fatal in the vast majority of cases. What is needed to combat gliomas is an avirulent virus which can be delivered to diseased tissue and can selectively replicate in and destroy malignant cells while sparing surrounding normal neural tissue. Such a treatment requires the use of a neurotrophic virus with radically attenuated virulence properties which is still capable of infecting the central nervous system. As Herpes simplex virus-1 (HSV-1) can replicate in the brain, this virus could be useful as a tumoricidal agent.

As an α-herpesvirus member of the family Herpesviridae, HSV-1 infection initiates in the oral cavity. While many primary infections are asymptomatic, limited replication in this peripheral, epithelial tissue ensues, followed by production of a cellular immune response. Some of the virus produced, however, migrates down axons which innervate this tissue and colonizes the neuronal cell bodies of the trigeminal ganglion. The virus persists here in a latent immunologically cloaked form for the life of the infected individual. Periodically, in response to stress or exposure to ultraviolet light, productive infection ensues in these neurons and mature virions migrate back down axons to the oral epithelia. A productive infection, or reactivation event, is initiated. The neutralization of virus produced in this episode and the fluid which accumulates form a fever blister or cold sore. This mild, benign condition afflicts millions worldwide. However, HSV-1 can also initiate a productive infection of the central nervous system. With a frequency of approximately 1 in 250,000, HSV-1 virions can reach the brain where infection can cause fatal encephalitis.

Neurovirulence of HSV-1 has been shown to be affected by mutations in a number of HSV open reading frames. Martuza in the published European Patent Application No. 0 514 603 describes the use of an HSV-1 mutant, dlsptk, as a means to destroy glioblastoma cells. A serious drawback of the dlsptk HSV-1 virus mutant is that this HSV-1 virus mutant can still cause fatal encephalitis. See, Markert, J. M., et al., Neurosurgery, 32:597–603 (1993); Chambers, R., et al., Proc. Natl. Acad. Sci. USA, 92:1411–1415 (1995).

A different type of mutation affecting neurovirulence has been described in Roizman U.S. Pat. No. 5,328,688 ("Roizman"), which is incorporated by reference herein in its entirety. Roizman describes HSV-1 mutants having mutations in both copies of the $\gamma_1 34.5$ gene to prevent the encoding of an active $\gamma_1 34.5$ gene product. Roizman's HSV-1 mutants are greatly attenuated in their neurovirulence properties. However, Roizman's $\gamma_1 34.5$ mutant viruses fail to grow in neuronal tumor tissue, making them poor candidates for a tumor specific agent capable of killing tumor cells. Chambers, R., et al., Proc. Natl. Acad., Sci. USA, 92:1411–1415 (1995). Roizman did find that one $\gamma_1 34.5$ mutant virus designated R4009 appeared to be more efficient than his other mutants in destroying neuronal tumor cells. R4009 inserts a stop codon in all three reading frames of the $\gamma_1 34.5$ open reading frame. The enhanced destruction of neuronal tumor tissue exhibited by R4009 can thus be due to a low level of $\gamma_1 34.5$ expression by "reading through" these stop codons. Chambers, R., et al., Proc. Natl. Acad., Sci. USA, 92:1411, 1415 (1995). This partial reconstruction of the wild-type phenotype illustrates the potential dangers of utilizing viruses which contain point mutations as therapeutic agents. Viruses which contain point mutations that impair their growth may eventually revert to wild-type and cause encephalitis.

In PCT Publication No. WO 96/00007, Martuza combined a ribonucleotide reductase mutation with Roizman's $\gamma_1 34.5$ deletion mutant virus designated R3616. Essentially, Martuza's approach does not differ from the studies described by Chambers, R., et. al., Proc. Natl. Acad. Sci. USA, 92:1411–1415 (1995). Like Roizman's $\gamma_1 34.5$ mutant virus described above, this double mutant virus would not be effective as an antineoplastic agent because this double mutant virus grows poorly in tumor tissue. Indeed, the ribonucleotide reductase mutation combined with the $\gamma 34.5$ mutation does not repair the profound growth defect of $\gamma 34.5$ mutant viruses on tumor tissue. To the contrary, this additional mutation serves to further cripple the virus, as evidenced by the enhanced sensitivity of this double mutant virus to gancyclovir. Another serious disadvantage of this double mutant virus is that the ribonucleotide reductase mutation is an insertion which could easily revert to yield a virus which contains only a $\gamma 34.5$ mutation. While a body of evidence exists supporting the notion that $\gamma 34.5$ mutant viruses are sufficiently attenuated to warrant safe intracranial administration, they are limited by the inability to grow efficiently and destroy neoplastic cells. It would thus be highly desirable to create a virus which retained the attenuation properties of the $\gamma 34.5$ mutant virus, but which would display selective, robust growth on malignant cells.

Accordingly, an object of the present invention is to provide viruses that are avirulent and can selectively replicate in tumor tissue, thereby having the capabilities of destroying a localized mass of tumor cells and sparing the surrounding normal tissue. A further object of the present invention is to provide a method of treatment of tumors employing these viruses. Another object of the present invention is to provide a vaccine protecting against herpes infections. These and other objects and features of the invention will be apparent from the following description.

SUMMARY OF THE INVENTION

The present invention provides a herpetic virus selected from the group consisting of neurotrophic herpes viruses, T-lymphotrophic viruses, and B-lymphotrophic viruses having a genome from which the gene or genes controlling virulence have been deleted and which requires at least one additional mutation to the genome, wherein the mutated herpetic virus is avirulent and selectively replicates in and destroys neoplastic cells. When the herpetic virus is a herpes simplex virus, the genes controlling virulence that are deleted are both copies of the $\gamma 34.5$ gene. Surprisingly, these herpetic viruses are both avirulent and able to selectively replicate in neoplastic cells. A pharmaceutical composition containing the herpetic virus mutant of the present invention is also provided.

An advantage of the herpetic virus mutant is that the virus destroys neoplastic cells without productively infecting surrounding normal, differentiated cells and generating a fatal infection of the central nervous system.

The present invention also provides a method for selectively destroying neoplastic cells in a mammal by administering to the mammal an effective amount of the herpetic virus of the present invention.

An advantage of this method is that an effective amount of the herpetic virus may be administered to a mammal to destroy neoplastic cells in the mammal without the danger of generating a fatal infection of the central nervous system.

The present invention further provides a vaccine for immunizing a mammal against herpetic viruses comprising the herpetic virus of the present invention and a pharmaceutically acceptable diluent, adjuvant or carrier, as well as a method of immunizing a mammal employing this vaccine.

An advantage of this vaccine is that the herpetic virus cannot cause a productive infection of the central nervous system of the recipient.

The present invention still further provides a method for isolating tumoricidal herpetic viruses by attenuating a herpetic virus to render it avirulent; identifying neoplastic cells which fail to support replication of the avirulent virus; sequentially passaging the attenuated virus on the neoplastic cells to produce isolates of the attenuated virus which can replicate in the neoplastic cells; and isolating the resulting viruses.

An advantage of this method is that the separation of the genetic neurovirulence determinants from the functions which enable the virus to replicate in neoplastic cells enables the selection of viruses which are avirulent and able to replicate in tumor cells, but not in normal, terminally differentiated cells.

Upon further study of the specification and appended claims, further objects and advantages of this invention will become apparent to those skilled in the art.

BRIEF DESCRIPTION OF THE DRAWINGS

FIGS. 6A–D are drawings which identify the nucleotide sequences in the BamHI Z fragment where the nucleotide sequences of the suppressor isolates deviate from the nucleotide sequences of wild-type HSV-1 (Patton strain). All the nucleotide numbers in FIGS. 6A–D correspond to the nucleotide numbers of the published sequence of strain 17, GENBANK accession number X14112D00317. FIG. 6A shows that for suppressor isolates SUP1 and SUP10, a deletion of 583 base pairs occurs in the BamHI Z fragment between nucleotide 145415 and nucleotide 145999. The base pairs flanking the deletion on the left are hereinafter designated SEQ ID NO: 1, and the base pairs flanking the deletion on the right are hereinafter designated SEQ ID NO: 2. FIG. 6B shows that for suppressor isolates SUP5 and SUP8, a deletion of 497 base pairs occurs in the BamHI Z fragment between nucleotide 145421 and nucleotide 145919. The base pairs flanking the deletion on the left are hereinafter designated SEQ ID NO: 3, and the base pairs flanking the deletion on the right are hereinafter designated SEQ ID NO:4. FIG. 6C shows for suppressor isolates SUP2 and SUP6 the occurrence of insertions of repetitive DNA elements along with deletions of genetic material. The base pairs on the left of checkboard rectangles are hereinafter designated SEQ ID NO: 5. There are two SUP6 in FIG. 6 because two SUP6 clones were obtained from one suppressor isolate. The checkerboard rectangles represent an iteration of HSV-1 sequences normally present from nucleotide numbers 145462 to 145477, hereinafter designated SEQ ID NO: 6. The small shaded oval represents HSV-1 sequences having nucleotide numbers 145481–145491, hereinafter designated SEQ ID NO: 7. The elongated shaded oval represents sequences which share homology to HSV-1 sequences contained in the repetitive portion of the viral genome. FIG. 6D shows for suppressor isolate SUP3 the occurrence of insertions of repetitive DNA elements along with deletions of genetic material. The elongated striped oval represents sequences which share homology to HSV-1 sequences contained in the repetitive portion of the viral genome. The base pairs to the left of the elongated striped oval are hereinafter designated SEQ ID NO: 8.

DETAILED DESCRIPTION OF THE INVENTION

Figure 1:
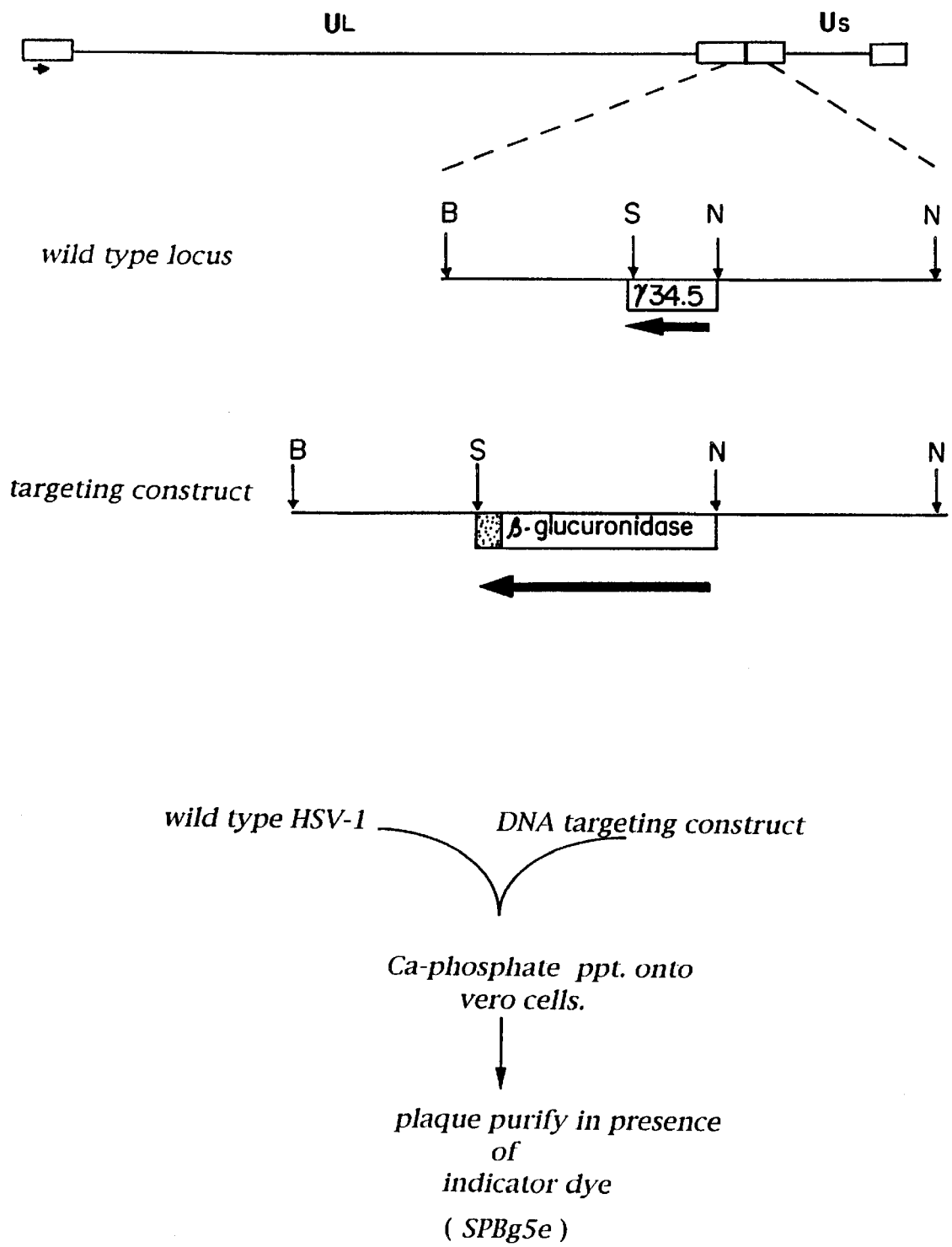
FIG. 1 is a schematic of the replacement of 34.5 coding sequences of HSV-1 with the β-glucuronidase gene. Letter abbreviations for restriction endonuclease cleavage sites are B=BamHI, S=SacI, and N=NcoI. $U_L$=Unique Long region of HSV-1. $U_S$=Unique Short region of HSV-1. The shaded region in the targeting construct at the 3' end of the β-glucuronidase gene represents the human cytomegalovirus Us10 polyadenylation site.

It is to be understood that while the present invention is primarily contemplated for humans, it is also contemplated for use in veterinary medicine.

The present invention provides a novel method for isolating herpetic viruses that are both avirulent and can replicate in neoplastic cells, but not in normal, differentiated cells, thereby having the capability to destroy a localized mass of neoplastic or tumor cells. Prior to the present invention, viruses have been rendered avirulent by different techniques. However, either the resulting avirulent viruses could not grow in tumor cells and therefore could not be used to destroy the tumor cells, or they were not attenuated sufficiently and were still capable of generating a productive infection in the central nervous system. For the first time, the functions of virulence and the ability to grow on tumor cells in a herpetic virus have been genetically separated and an avirulent herpetic virus has been produced which can grow in tumor cells.

In the method for isolating tumoricidal herpetic viruses, the herpetic virus is attenuated to render it avirulent. The herpetic virus is preferably a neurotrophic virus, a B-lymphotrophic virus, or a T-lymphotrophic virus. The neurotrophic virus is preferably a herpes simplex virus and is more preferably HSV-1, HSV-2, or Varicella-zoster virus (VZV). The T-lymphotrophic virus is preferably human herpes virus-6 (HHV-6). The B-lymphotrophic virus is preferably Epstein-Barr virus. The herpetic virus is rendered avirulent by altering the gene or genes controlling virulence using techniques known in the art which include point mutations (substitutions), insertions or deletions to the gene or genes. It is preferred to render the herpetic virus avirulent by completely deleting the gene or genes controlling virulence to minimize the possibility of reversion to a virulent form of the wild-type virus. When the herpetic virus is a herpes simplex virus, both copies of the γ34.5 gene are completely deleted.

The next step in the method is to identify a neoplastic cell that will not support replication or will support, at most, limited replication of the avirulent herpetic virus as compared to replication of the wild-type herpetic virus in the neoplastic cell. Such neoplastic cells include cells of tumors, carcinomas, sarcomas, leukemia, lymphomas, and the like. Nervous system tumors include astrocytomas, oligodendrogliomas, meningiomas, neurofibromas, ependymomas, Schwannomas, neurofibrosarcomas, and gliomas such as glioblastomas.

Once the neoplastic cell is identified, the avirulent virus is sequentially passaged on the identified neoplastic cell until viral isolates are produced which display efficient, productive growth compared to the starting avirulent parent virus (which does not grow in neoplastic cells). The sequential passaging is carried out by infecting neoplastic cells either just confluent or approaching confluence with avirulent virus at multiplicities of infection of $10^{-1}$ to $10^{-4.}$ Cultures are examined each day for signs of cytopathic effect. When the cultures displayed either complete cytopathic effect or the neoplastic cells have completely exhausted the media, a lysate is prepared by freeze-thawing and sonicating for approximately one minute in a water bath. A second culture of neoplastic cells is infected with 0.1 ml of the lysate and the entire passaging process repeated four times in succession. Those cultures which are capable of generating substantial cytopathic effect on the neoplastic cells prior to the cells exhausting the media are isolated and subjected to two rounds of plaque purification. Large scale stocks are then prepared on the neoplastic cells.

Only those avirulent viruses that have regained the ability to grow on the identified neoplastic cell will replicate in those neoplastic cells and form isolates from which these viruses can be obtained. To regain the ability to grow on the identified neoplastic cell, at least one additional mutation must occur to the genome of the herpetic virus. When the avirulent virus is a herpes simplex virus, at least one of the additional mutations to the gene may affect the nucleotide sequence between BstEII (corresponding to nucleotide number 145316 of the published sequence of strain 17, GENBANK accession number X14112D00317) and NcoI (corresponding to nucleotide number 146592 of the published sequence of strain 17, GENBANK accession number X14112D00317) of the BamHI Z fragment of HSV-1. As this isolate has sustained a mutation at a site distinct from the $\gamma34.5$ genes, it is a second-site suppressor mutant, also referred to as a suppressor isolate, which rescues the growth defect of $\gamma34.5$ deletion viruses on neoplastic neuronal cells.

A sample of a HSV-1 suppressor isolate in accordance with the present invention, designated SUP1, has been deposited under the terms of the Budapest Treaty with the American Type Culture Collection (ATCC) at 12301 Parklawn Drive, Rockville, Md. 20852 USA under Accession Number ATCC VR-2510.

The isolated avirulent herpetic virus is used to destroy neoplastic cells in a mammal because of its ability to infect and replicate in such neoplastic cells. Administration of the herpetic viral isolate to a mammal in an effective amount provides circulating virus which enters a mass of malignant tumor cells and initiates and propagates an infection in the malignant cells which results in their destruction. Alternatively, the herpetic viral isolate is injected into the mammal at or near the site of neoplastic growth. The amount of virus to be administered ranges in concentration from about $10^1$ to about $10^{10}$ plaque forming units (pfu), preferably from about $5\times10^4$ pfu to $1\times10^6$ pfu, and more preferably from about $1\times10^5$ to about $4\times10^5$ pfu, although the most effective ranges may vary from host to host. When the neoplastic cells to be destroyed are glioma cells, the preferred isolated herpetic virus is a herpes simplex virus such as HSV-1 or HSV-2 having both copies of the $\gamma34.5$ gene deleted and an additional mutation enabling the herpes simplex virus to selectively replicate in the glioma cells. The HSV-1 suppressor isolate (SUP1) deposited under ATCC Accession Number VR-2510 is used in this method of destroying neoplastic cells.

A pharmaceutical composition containing the isolated herpetic virus is used for treating tumors in a mammal. The pharmaceutical composition comprises the isolated herpetic virus of the present invention and a pharmaceutically acceptable carrier, adjuvant or diluent. The pharmaceutical composition may be in injectable form.

The isolated herpetic viruses of the present invention are also employed as a vaccine against herpetic viruses when combined with a pharmaceutically acceptable diluent, adjuvant, or carrier. A mammalian host, preferably human, is inoculated with a vaccine comprising an immunity-inducing dose of one or more of the live vaccinal herpetic viral strains of the invention by the parenteral route, preferably by intramuscular or subcutaneous injection. Inoculation may also be effected by surface scarification, or by inoculation of a body cavity. Typically, one or several inoculations of between about 10 and 1,000,000 pfu each, as measured in susceptible human or nonhuman primate cell lines, are sufficient to effect immunization of a human host.

The vaccine may be conveniently utilized in liquid form or in freeze-dried form, in the latter case in combination with one or more suitable preservative and protective agents to protect the vaccinal strains during the freeze-drying process.

In a preferred embodiment, a recombinant HSV-1 virus (strain Patton) was created where both copies of the $\gamma34.5$ gene were replaced by DNA sequences encoding $\beta$-glucuronidase, as illustrated by FIG. 1. Briefly, FIG. 1 shows a schematic drawing of the HSV-1 genome highlighting the locations of both copies of the $\gamma34.5$ gene in a repetitive region of the genome. The targeting construct shown in FIG. 1 is a plasmid which targets the $\beta$-glucuronidase gene to the 34.5 genetic locus. The plasmid was created by cloning the HSV-1 sequences which normally bracket the 34.5 gene into the corresponding positions so as to surround the $\beta$-glucuronidase gene. After cotransfecting the targeting construct along with wild-type HSV-1 DNA onto Vero cells by the calcium-phosphate precipitate (Ca-phosphate ppt.) technique, recombinant virus, designated the parental SPBg5e virus, was isolated by plaque purification in the presence of indicator dye or calorimetric substrate to facilitate the identification of recombinant plaques on Vero cells.

Figure 3:
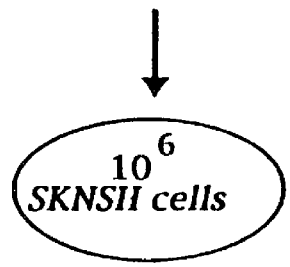
FIG. 3 is a drawing presenting results of a growth analysis of a selected suppressor isolate. pfu=plaque forming units. Δ34.5=SPBg5e virus. wt=wild-type HSV-1 Patton strain. REV 4=a suppressor isolate.

SKNSH neuroblastoma cells, obtained from the ATCC, are non-permissive for the growth of 34.5 HSV-1 mutants. Presumably, this reduction in viral growth reflects the fact that all protein synthesis ceases with the onset of viral DNA replication. See, Chou, J. and Roizman, B., Proc. Natl. Acad. Sci. USA, 89:3266–3270 (1992). The recombinant HSV-1 mutant designated SPBg5e also failed to synthesize wild-type levels of late proteins on SKNSH cells. The premature termination of protein synthesis in neuroblastoma cells infected with this 34.5 deletion mutant causes a dramatic reduction in viral yield. FIG. 3 shows the difference in yield between the 34.5 deletion mutant ($\Delta34.5$) and the wild-type (wt) virus. For example, at 100 pfu, the difference in yield is 56,000 fold. This growth defect was employed as and found to be a powerful means for biological selection to isolate second-site suppressor mutants.

Figure 2:
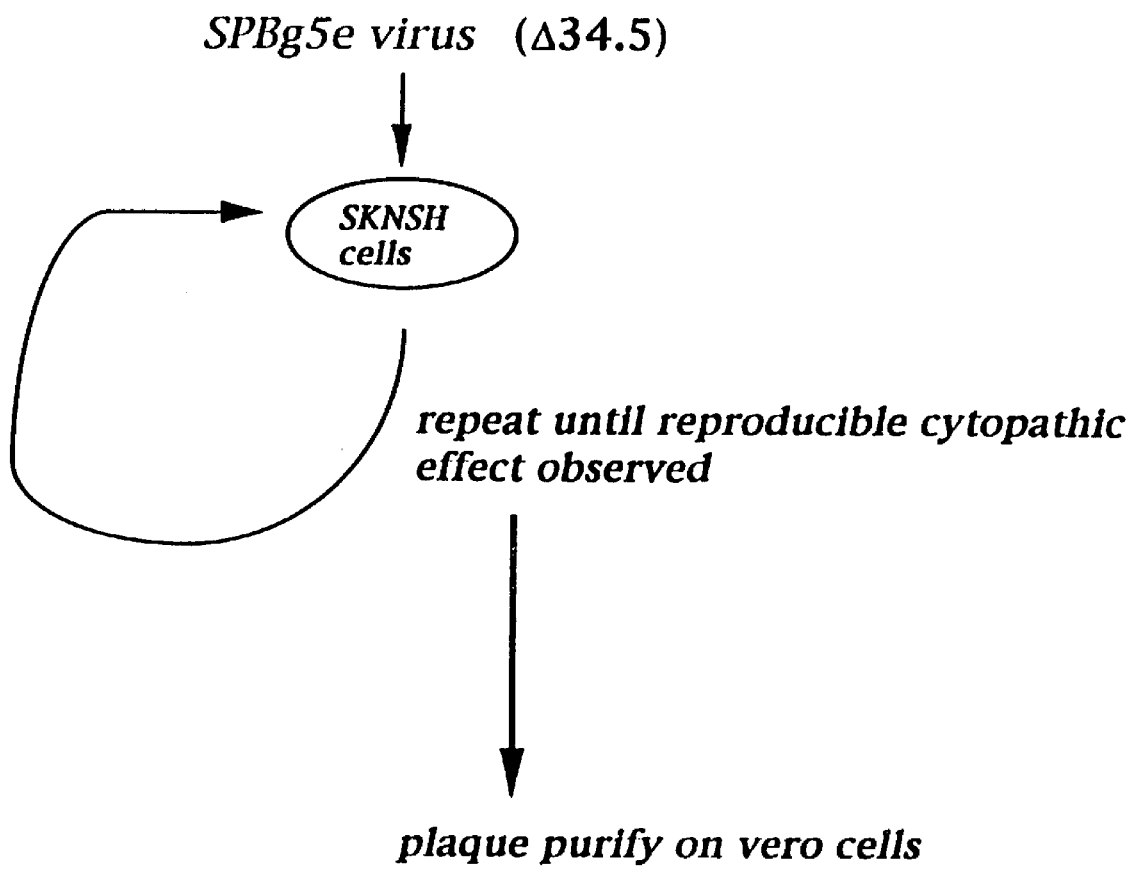
FIG. 2 is a schematic of the isolation of second-site suppressor mutants from parental SPBg5e 34.5 deletion (Δ34.5) stocks.

The parental SPBg5e virus, which completely lacked all coding sequences for the 34.5 gene, was passaged multiple times in succession on SKNSH neuroblastoma cells, as illustrated in FIG. 2. Multiple plaque-purified independent isolates were capable of sustained protein synthesis and growth on cells of neuronal origin, notably SKNSH neuroblastoma and U373 human glioblastoma (see FIGS. 3 and 7). FIG. 3 is a schematic outlining the procedure to analyze the growth of selected suppressor isolates on SKNSH cells at different multiplicities of infection. FIG. 3 shows as an example, either 10, 100, or 1,000 pfu of wild-type HSV-1, $\Delta34.5$ mutant (SPBg5e), or REV4 (a suppressor isolate in accordance with the present invention) were used to infect SKNSH cells. After incubating 48 hours at 37° C., a lysate was obtained by freeze thawing and the viral titer was determined on Vero cells. At all multiplicities of infection examined, the suppressor isolate REV4 grew 50 to 100 times better than the parental $\Delta34.5$ deletion mutant on SKNSH cells. Analysis of viral DNA revealed that all of the suppressors rearranged a region of the BamHI Z fragment of HSV-1 (Patton strain) where the Unique Short component joins the Short Terminal Repeat. These mutations affect the cis-acting sequences which direct transcription of the Us11 open reading frame and disrupt the coding region of the Us12 open reading frame (see FIG. 5). Analysis of viral proteins produced late in infection confirmed that the Us11 protein is either not produced or is produced at enormously reduced levels (see FIG. 7).

The genetic rearrangements most likely affect one or more components of a signaling pathway which involves the protein encoded by the γ34.5 gene. In the absence of the 34.5 gene product, the virus presumably generates a signal which leads to the cessation of protein synthesis. This inhibition of translation leads to the death of the infected cell prior to the assembly of optimal amounts of infectious progeny. The γ34.5 gene encodes a factor which fosters the survival of the infected cell and the assembly and dissemination of infectious virus. The combined absence of the signal which potentiates the shutdown of translation and the deletion of the 34.5 neuronal survival function creates a novel virus which can efficiently replicate in malignant glioblastoma tissue, but does not cause-fatal encephalitis. As all 34.5 coding sequences are deleted in the viruses of this embodiment of the invention, it is not possible to reconstruct the wild-type phenotype by producing small amounts of the 34.5 gene product, thereby avoiding infection of the central nervous system. Novel genetic changes have occurred in these isolates which restore the ability of the virus to grow productively on neoplastic cells. The method of the present invention results in the separation of the genetic neurovirulence determinants from the functions which enable the virus to replicate in neoplastic cells.

The present invention demonstrates for the first time that it is possible for a non-neurovirulent herpetic virus unable to productively grow on neoplastic cells to reacquire the ability to productively grow on neoplastic cells without reacquiring a neurovirulent phenotype. When herpes simplex virus has a single genetic element, the γ34.5 gene, deleted, the herpes simplex virus loses its neurovirulence, but also loses the ability to replicate in neoplastic neuronal cells SKNSH and U373. The present invention has solved this problem by providing a novel herpes simplex virus from which the γ34.5 gene has been deleted and which contains a mutation in a different genetic element that restores the virus' ability to replicate in neoplastic neuronal cells, including SKNSH and U373 cells, but retains the non-neurovirulent phenotype.

Without being bound by theory, it is believed that inoculation of these 34.5 suppressor isolates intracranially into brains afflicted with glioblastoma results in the selective destruction of malignant tissue. When the virus destroys a mass of tumor cells and encounters normal brain tissue, a self-limiting infection is initiated at this peripheral zone which curtails the spread of infectious virus. As these isolates can replicate in glioblastoma cells, a limiting feature of the 34.5 deletion mutants described by Roizman, which do not replicate in glioblastoma cells, has been overcome. Since the suppressor isolates replicate efficiently in glioblastoma cells, small amounts of circulating virus which enter a mass of malignant cells are able to initiate and propagate an infection solely in the malignant cells. One possible explanation for the suppressor isolates' ability to replicate in glioblastoma cells is that the suppressor mutants are now dependent on the proliferative capacity of their host cell, and have lost the ability to grow efficiently on cells which are terminally differentiated. Since malignant cells have shed their terminally differentiated phenotype, they are now suitable hosts for the growth of the suppressor mutants.

In the event that viral titers in tumor masses reach potentially dangerous levels, the infection can be controlled by administering an anti-viral compound such as acyclovir, as all these suppressor viruses have a wild-type thymidine kinase (tk) gene. Their replication activity can be further curtailed by combining mutations in other non-essential replicative functions, for example, ribonucleotide reductase, into the suppressor genome. This imposes a limit on the titer of replicating virus in the vicinity of the tumor mass and provides additional host specificity for actively dividing cells, as the complementing cellular enzyme is under stringent cell-cycle control.

The additional mutation to the suppressor isolates also disrupt the Us12 open reading frame. The protein product encoded by Us12 is the α47 immediate early polypeptide. As this protein product accumulates at early times post-infection, it would need to have a previously undescribed late function for it to be involved in the premature termination of late protein synthesis. The α47 polypeptide has been shown to down regulate expression of cellular class I MHC molecules in infected cells, and as such is an important modulator of the immune system. The fact that cells infected with suppressor isolates display functional MHC class I molecules on their surface implies that viral antigen presentation may be up-regulated in these cells (relative to those infected with a virus which carries a wild-type allele of α47). The presence of viral antigens on the surface of tumor cells may further facilitate tumor destruction by components of the host immune system.

Additionally, these suppressor isolates are useful as potential vaccine strains. Like the parental 34.5 deletion mutants, the suppressor isolates do not infect the central nervous system and cause encephalitis. Since the suppressor isolates of the present invention replicate better than the parental 34.5 deletion mutants in some cultured cells, it is expected that the suppressor isolates would also replicate better than parental 34.5 deletion mutants in peripheral tissue and thus elicit the requisite immune response capable of inducing productive immunity.

In order that this invention may be better understood, the following examples are set forth. The examples are for the purposes of illustration only and are not to be construed as limiting the scope of the invention.

EXAMPLES

Example 1

Replacement of HSV-1 34.5 Coding Sequences With β-glucuronidase Gene

The plasmid pBgdUs10, described in Jones, T., et al., J. Virol., 65:5860–5872 (1991), was digested with ApaI, end filled with Klenow polymerase, and subsequently digested with XbaI. The 2.1 kb fragment which contains the β-glucuronidase gene (available from Clontech, San Diego, Calif. as pRAJ275b) fused to the human cytomegalovirus Us10 polyadenylation site (an ApaI-SmaI fragment corresponding to human cytomegalovirus strain AD169 nucleotide numbers 13527–13782; GENBANK accession number X04650) at its 3' border, was isolated and cloned into pT7-1 (U.S. Biochemical, Cleveland, Ohio) which had been digested with XbaI and SmaI to create pBg10pA. The HSV-1 (Patton strain) BamHI SP fragment (corresponding to nucleotide numbers 123459–129403 in the published sequence of strain 17, GENBANK accession number X14112D00317), described in Jones, T. R. and Hyman, R. W., Virology, 131:555–560 (1983), was cloned into the BamHI site of pBR322 and digested with NcoI. The 1.8 kb NcoI fragment (corresponding to nucleotide numbers 127666–125855 in the published sequence of strain 17, GENBANK accession number X14112D00317) which contains the promoter and the first ATG codon of the 34.5 gene was isolated and cloned into NcoI digested pBg10pA. This plasmid (p5'γ34.5Bg10pA) was digested with EcoRI, end-filled with Klenow polymerase, and then digested with SacI. The HSV-1 BamHI SP clone was digested with BamHI, end filled with Klenow polymerase, and digested with SacI. The 1.6 kb terminal SacI-BamHI (Klenow filled) fragment (corresponding to nucleotide numbers 123459–125066 in the published strain 17 sequence, GENBANK accession number X14112D00317) was isolated and ligated into EcoRI (Klenow filled)/SacI digested p5'γ34.5 Bg10pA to create p5'γ34.53'γ34.5, which has been abbreviated as pSPBg. This plasmid places the β-glucuronidase gene under the control of the endogenous 34.5 promoter and surrounds the β-glucuronidase gene with HSV-1 sequences which normally flank the 34.5 gene. Five μg of purified plasmid (linearized with HindIII), 2 μg of purified HSV-1 (Patton strain) DNA and sonicated salmon sperm DNA carrier were assembled and introduced into Vero cells by the calcium-phosphate technique. Once the cytopathic effect had progressed throughout the monolayer, a lysate was obtained by freeze-thawing, followed by a one minute burst in a water bath sonicator. Dilutions were prepared and isolates were subjected to two rounds of plaque purification on Vero cells in the presence of the indicator dye X-gluc. The isolate used in subsequent studies was designated SPBg5e. Restriction digestion and Southern analysis demonstrated that the gene for β-glucuronidase had replaced both copies of the 34.5 gene.

Example 2

Selection Procedure to Obtain Suppressor Mutants

Sixty mm dishes of SKNSH neuroblastoma cells which were either just confluent, or approaching confluence, were placed in DMEM plus 2% fetal bovine serum (FBS) and infected with SPBg5e at multiplicities of infection of $10^{-1}$ to $10^{-4}$. Cultures were examined each day for signs of cytopathic effect. Generally, the cultures displayed either complete cytopathic effect (at higher multiplicities of infection) or the neuroblastoma cells had completely exhausted the media by five to seven days post infection. At this point, a lysate was prepared by freeze-thawing, sonicated for one minute in a water bath, and 0.1 ml of this lysate was used to infect a second 60 mm dish. This process was repeated four times in succession. At this time, some of the cultures were capable of generating substantial cytopathic effect on SKNSH prior to the cells exhausting the media. Isolates were then subjected to two rounds of plaque purification on Vero cells, and large scale stocks were then prepared on SKNSH cells. Staining of the plaques with X-gluc revealed that the isolated plaques retained the β-glucuronidase gene of the parental virus and were capable of growth on both Vero and SKNSH cells.

Example 3

Analysis of Viral DNA From Suppressor Isolates

Stocks of suppressor isolates prepared on SKNSH cells prepared by the procedures of Example 2 were used to infect Vero cells at a multiplicity of infection of one. Infected cell cultures were maintained in Media 199 (m 199)(Gibco BRL, Bethesda, Md.) plus 1% calf serum and incubated at 34° C. until maximum cytopathic effect was observed. Cells were harvested, suspended in 10 mM Tris, pH 8.4, 140 mM NaCl, 10 mM MgCl$_2$, and lysed by addition of the same buffer containing 1% Triton X-100™. After sitting five minutes on ice, the extracts were centrifuged at 14,000×g for two minutes. The supernatant (removed with a wide bore tip) was adjusted to a final concentration of 0.4% SDS, 10 mM EDTA, 25 μg/ml RNase A, 1 mg/ml Pronase and incubated for at least one hour at 37° C. DNA was purified by two extractions with phenol:chloroform, one extraction with chloroform, and then precipitated with ethanol. Following a wash with 70% ETOH, the pellet was allowed to dry at room temperature, and resuspended in 10 mM Tris-HCl, pH 8.0, 0.1 mM EDTA. These minipreparations of viral DNA yielded adequate amounts for molecular cloning.

At first, viral DNA was cloned as a series of EcoRI fragments into EcoRI digested pBR322. Restriction digests and Southern analysis established that the breakpoints appeared to be confined in the BamHI Z fragment (corresponding to nucleotide numbers 144875–146828 in the published strain 17 sequence, GENBANK accession number X14112D00317). To subsequently isolate BamHI Z fragments, viral DNA was digested with BamHI and fragments which migrated between 1 and 3 kb were size selected by agarose gel electrophoresis, purified, and cloned into BamHI-digested pBR322. Clones containing BamHI Z inserts were identified by colony hybridization, and confirmed by Southern blotting. BamHI Z fragments from the suppressor isolates were digested with a variety of single cut enzymes to map the extent of the deletion. As all of the isolates retained the BstEII site contained within the unique portion of BamHI Z, a sequencing primer was designed to read from this point towards the repetitive region. The sequencing primer had the following sequence:

5' CCCTCCGCCCAGAGACTCG 3'

The sequence of the sequencing primer corresponds to nucleotide numbers 145270–145288 in the published sequence of strain 17 (GENBANK accession number X14112D00317) and is hereinafter designated SEQ ID NO: 9. DNA sequencing was performed using a USB Sequenase™ kit (U.S. Biochemical, Cleveland, Ohio) according to the manufacturer's instructions.

Figure 4:
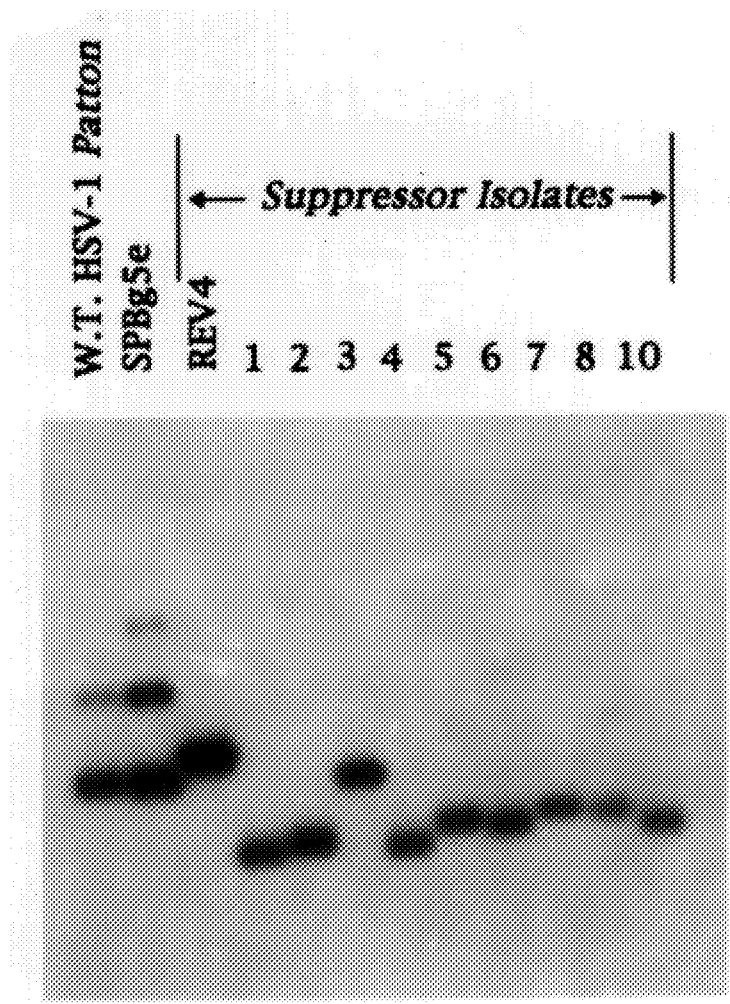
FIG. 4 is an autoradiograph of a Southern blot detailing the genetic structure of the BamHI Z fragment of suppressor isolates 1 to 8 and 10 and REV4; 34.5 deletion mutant SPBg53e; and wild-type (W.T.) HSV-1 (Patton strain).

FIG. 4 is an autoradiograph of a Southern blot where DNA from suppressor isolates SUP1 to 8, SUP10, and REV4; 34.5 deletion mutant SPBg5e; and wild-type HSV-1 (Patton strain) were prepared as described above in Example 3 and digested with BamHI. After separating the fragments by agarose gel electrophoresis and blotting, the membrane was probed with a $^{32}$P-labeled BamHI-BstEII fragment corresponding to the Unique portion of the BamHI Z fragment (corresponding to nucleotide numbers 144875–145316 in the published sequence of strain 17, GENBANK accession number X14112D00317). Restriction digestion and Southern analysis of each isolate demonstrated that all of the suppressors had a DNA rearrangement. In one isolate (REV4), a complex inversion occurred, while all of the others involved deletions or insertions (see FIG. 4).

Figure 5:
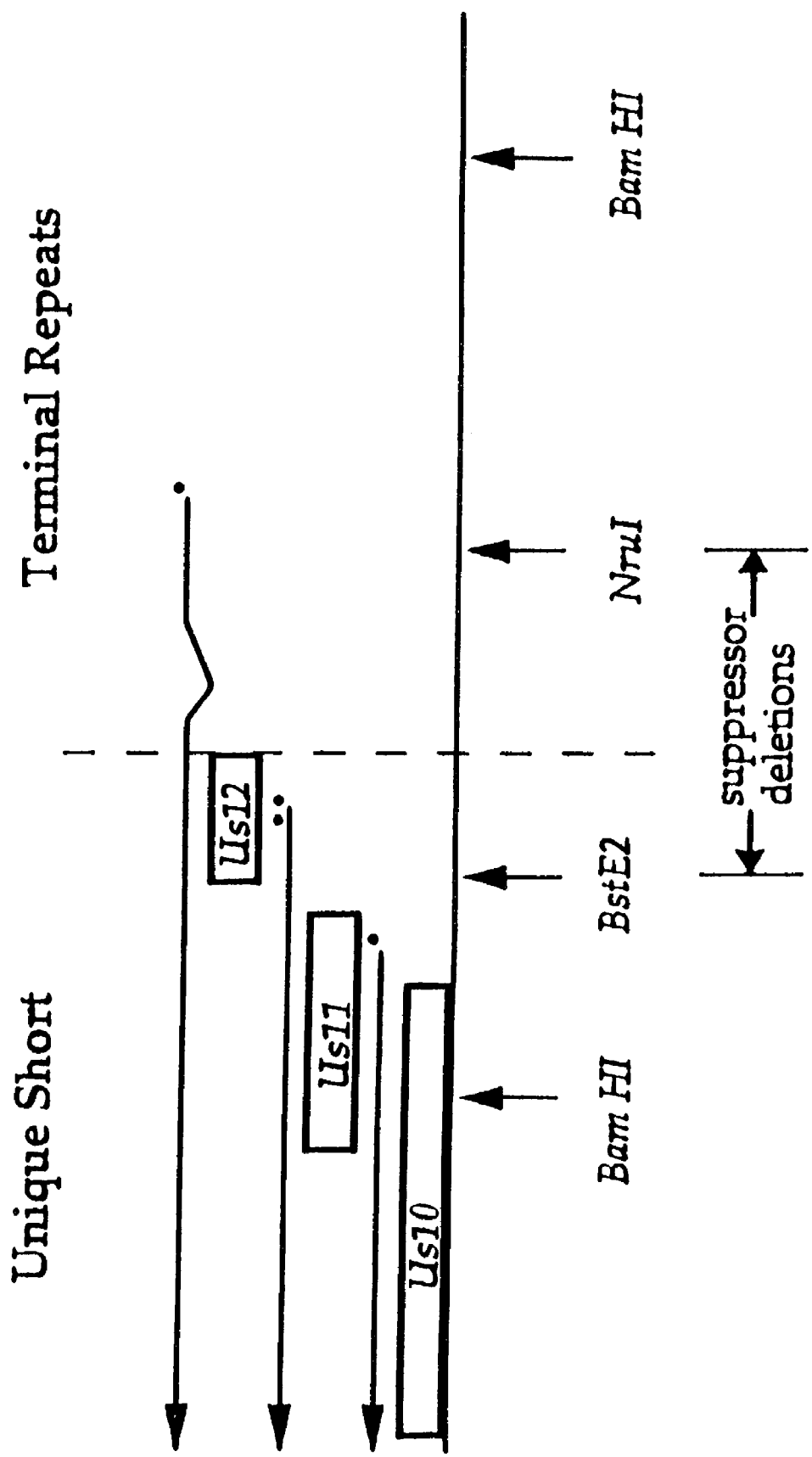
FIG. 5 is a drawing highlighting the junction between the Unique Short region and the Short Terminal Repeats of the BamHI Z fragment in wild-type HSV-1.

The BamHI Z fragment from each of several suppressor isolates, including those identified in FIG. 4, was isolated by molecular cloning techniques as described above in Example 3. Although the 440 bp BamHI-BstEII Unique Short piece was wild-type by restriction analysis, it was evident that a rearrangement had occurred in all of the isolates between the BstEII site and the EcoRI site. FIG. 5 shows a physical map of a segment of the wild-type BamHI Z fragment which begins at the BamHI site in the Unique Short region and extends through the Nru site in the Short Terminal Repeats (corresponding to nucleotide numbers 144875–146008 of the published sequence of strain 17, GENBANK accession number X14112D00317). The sequencing primer having the sequence 5' CCCTCCGC-CCAGAGACTCG 3'(SEQ ID NO: 9) was designed to read from the BstEII site towards the end of the Unique Short sequences. The sequencing was performed as described above. The points at which the sequences of the suppressor isolates deviated in the BamHI Z fragment from wild-type HSV-1 were identified and are displayed in FIG. 6.

Figure 6D:
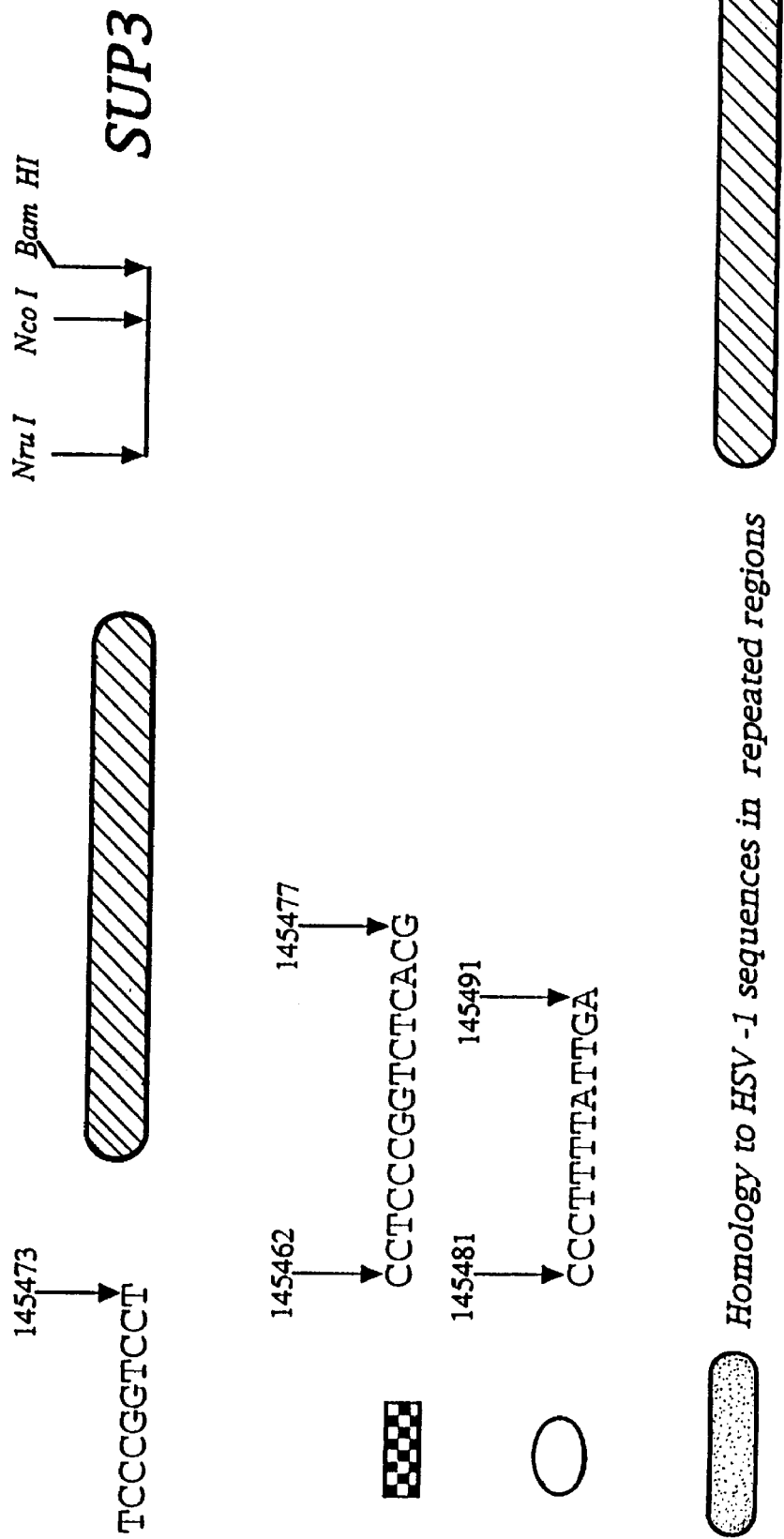

FIGS. 6A–D identify the nucleotide sequences in the BamHI Z fragment where the nucleotide sequences of the suppressor isolates deviate from the nucleotide sequences of wild-type HSV-1 (Patton strain). All the nucleotide numbers in FIGS. 6A–D correspond to the nucleotide numbers of the published sequence of strain 17, GENBANK accession number X14112D00317. As shown in FIG. 6A, a deletion of 583 base pairs occurs in the BamHI Z fragment between nucleotide 145415 and nucleotide 145999 of suppressor isolates SUP1 and SUP10. As shown in FIG. 6B, a deletion of 497 base pairs occurs in the BamHI Z fragment between nucleotide 145421 and nucleotide 145919 of suppressor isolates SUP5 and SUP8. As shown in FIG. 6C, insertions of repetitive DNA elements along with deletions of genetic material occurs in suppressor isolates SUP2 and SUP6. The point at which the nucleotide sequence of the suppressor isolate deviates from the nucleotide sequence of wild-type HSV-1 (Patton strain) in the BamHI Z fragment is nucleotide 145477. There are iterations of HSV-1 sequences normally present from nucleotide numbers 145462 to 145477 (SEQ ID NO: 6); HSV-1 sequences having nucleotide numbers 145481–145491 (SEQ ID NO: 7); and sequences which share homology to HSV-1 sequences contained in the repetitive portion of the viral genome. The nucleotide sequence of the more distal junction is not yet known. As shown in FIG. 6D, insertions of repetitive DNA elements along with deletions of genetic material occur in suppressor isolate SUP3. The point at which the nucleotide sequence of the suppressor isolate deviates from the nucleotide sequence of wild-type HSV-1 (Patton strain) in the BamHI Z fragment is nucleotide 145473. There are sequences which share homology to HSV-1 sequences contained in the repetitive portion of the viral genome. The nucleotide sequence of the more distal junction is not yet known.

Analysis of this sequencing data revealed that all of the suppressors shared the common characteristic of a rearrangement in a region of the BamHI Z fragment of HSV-1 (Patton strain) where the Unique Short component joins the Short Terminal Repeat. These mutations affect the cis-acting sequences which direct transcription of the Us11 open reading frame and disrupt the coding region of the Us12 open reading frame (see FIG. 5). Analysis of viral proteins produced late in infection confirmed that the Us11 protein is either not produced or is produced at enormously reduced levels (see FIG. 7). The genetic rearrangements most likely affect one or more components of a signaling pathway which involves the protein encoded by the γ34.5 gene.

Example 4
Analysis of Total Viral Protein Synthesis

U373 human glioblastoma cells, obtained from the ATCC, were infected with either SPBg5e (34.5 deletion mutant), wild-type HSV-1 (Patton strain), or suppressor isolates SUP10 and SUP4 at a multiplicity of infection of approximately ten, or infected with suppressor isolate REV4 at a multiplicity of infection of one for approximately one hour at 37° C. The cells were then refed with DMEM plus 2% FBS and allowed to incubate overnight. At any point after 12 hour post-infection (usually 15.5 hours), the infected cells were overlaid with one ml of DMEM containing 50–70 $\mu$Ci/ml $^{35}$S Express™ (a commercial mixture of methionine and cysteine from DuPont New England Nuclear, Boston, Mass.) and the incubation continued for one hour. Total cellular protein was solubilized in 1×Laemli buffer, boiled for three minutes, and a portion was fractionated on 12.5% SDS-polyacrylamide gels. There were also separate lanes in the gel for uninfected U373 cells and for a $C^{14}$-labeled high molecular mixture weight (MW) from Amersham as molecular weight markers for comparative purposes. Gels were fixed in 25% MeOH, 10% acetic acid, dried, and exposed to Kodak XAR film.

Figure 7:
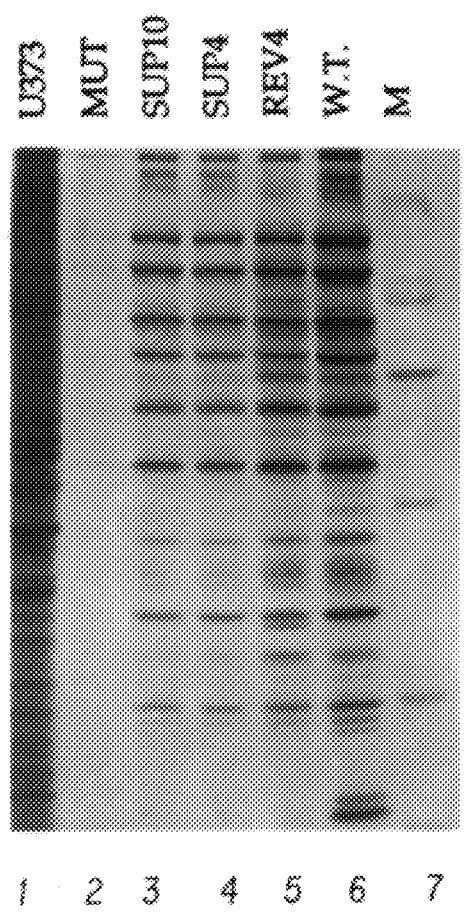
FIG. 7 is an autoradiograph of an SDS polyacrylamide gel which displays proteins synthesized at late times post-infection by selected suppressor isolates on U373 human glioblastoma cells. Lane 1 is uninfected U373 human glioblastoma cells (U373). Lane 2 is SPBg5e virus (MUT). Lane 3 is suppressor isolate SUP10. Lane 4 is suppressor isolate SUP4. Lane 5 is suppressor isolate REV4. Lane 6 is wild-type HSV-1 Patton strain (W.T.). Lane 7 is molecular weight markers (M).

The results are displayed in FIG. 7. FIG. 7 is an autoradiograph of an SDS polyacrylamide gel which displays viral proteins produced at late times post infection in U373 cells infected with either the Δ34.5 mutant (MUT), the suppressor isolates SUP10, SUP4, or REV4, or wild-type HSV-1 (W.T.). While infection of U373 cells with the 34.5 deletion mutant results in the cessation of protein synthesis, the suppressor isolates are capable of sustained protein synthesis on these cells.

Example 5
Neurovirulence Assay

Figure 8:
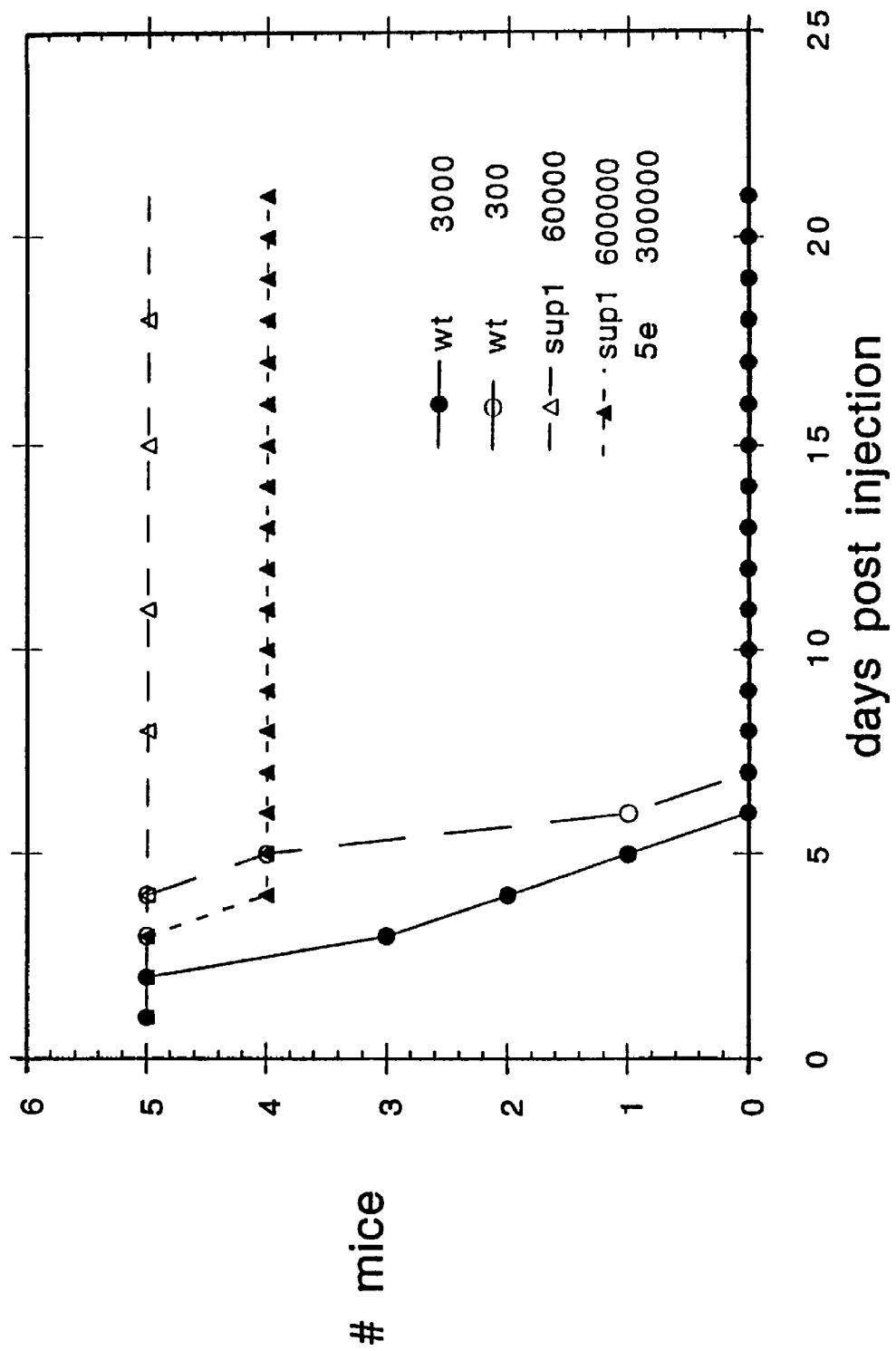
FIG. 8 is a graph displaying survival results of mice injected intracranially with different amounts of suppressor isolate SUP1, SPBg5e Δ34.5 mutant (5e), or wild-type HSV-1 Patton strain (wt). ●=3,000 pfu wild-type HSV-1 Patton strain. ○=300 pfu wild-type HSV-1 Patton strain. Δ=60,000 pfu suppressor isolate SUP1. ▲=300,000 pfu SPBg5e Δ34.5 mutant virus and ▲=600,000 pfu suppressor isolate SUP1, as the data was identical for each.

Wild-type HSV-1 virus, SPBg5e 34.5 deletion mutant virus, and suppressor isolate SUP1 were each diluted in DMEM plus 1% calf serum. Particulate matter was removed from viral stocks by a brief spin in a microfuge prior to dilution. Twenty-one day old female Balb/C mice (Charles River Laboratories, Mass.) were inoculated intracranially with 30 $\mu$l of diluted virus. The mice, in groups of five, were injected intracranially with either 300 or 3,000 pfu of wild-type HSV-1 (wt); 300,000 pfu of SPBg5e; or 60,000 or 600,000 pfu of suppressor isolate (SUP1). After injection, the mice were followed for 21 days and scored for survival. The results are illustrated in FIG. 8. All the mice injected with 300 or 3,000 pfu of wild-type virus died. In contrast, the mice injected with the suppressor isolate SUP1 survived, as well as the mice injected with the non-neurovirulent 34.5 deletion mutant. The neurovirulence properties of the suppressor isolate SUP1 were identical to the neurovirulence properties of the 34.5 deletion mutant.

Example 6
Marker Rescue Analysis

Multiple, independent isolates were obtained with breakpoints clustering in the same region, suggesting that this rearrangement was a necessary component of the suppressor phenotype. To prove that it was both necessary and sufficient to confer this phenotype on γ34.5 mutant viruses, marker rescue experiments were performed.

Figure 9:
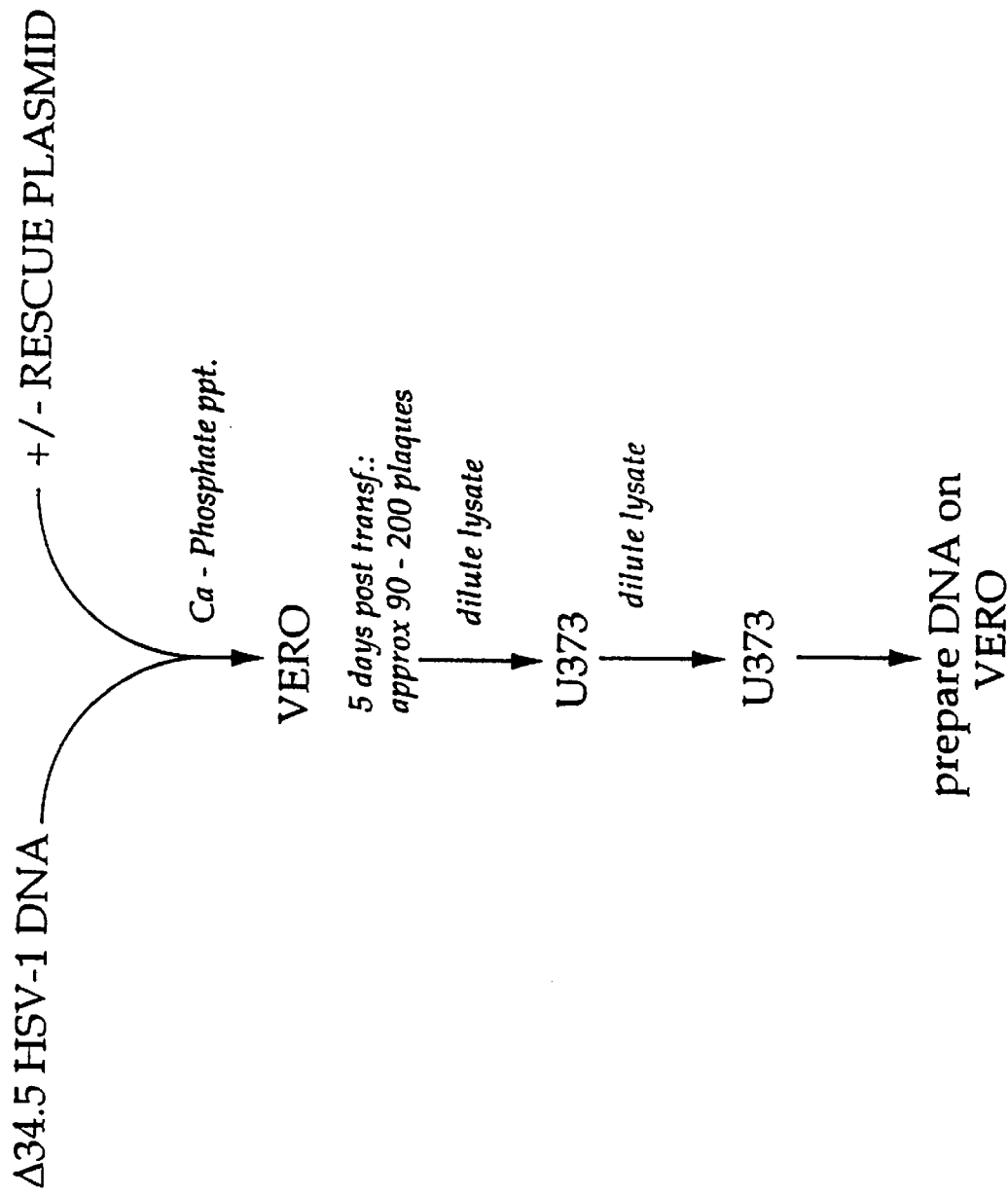
FIG. 9 is a schematic of the experimental technique used to rescue the suppressor phenotype of the second-site suppressor mutants.

The rearranged regions in all but one SUP6 clone were contained completely between the BstEII and NruI sites. These rearranged BstEII-NruI fragments were then used to replace the wild-type BstEII-NruI fragment in the targeting vector pSXZY. The insert in pSXZY contains HSV-1 Patton strain sequences from the SalI site at nucleotide 143481 to the BstEII site at 147040. The nucleotide coordinates refer to the published sequence of HSV-1 strain 17, GENBANK accession number X14112D00317. This insert was cloned between the unique SalI and HindIII sites in the vector pGEM9zf-(Promega, Wis.). As the BstEII site at 147040 and the unique HindIII site in pGEM9zf- were end-filled by prior treatment with the Klenow fragment of DNA polymerase 1, both sites were destroyed. pSXZY thus has unique BstEII sites and NruI sites to facilitate the exchange of BstEII - NruI fragments from the BamHI Z region. The flanking sequences, which extend in either direction from the internal BstEII - NruI fragment, function to direct homologous recombination within this region of the viral chromosome. FIG. 9 illustrates the experimental approach employed to rescue the suppressor phenotype.

Figure 10:
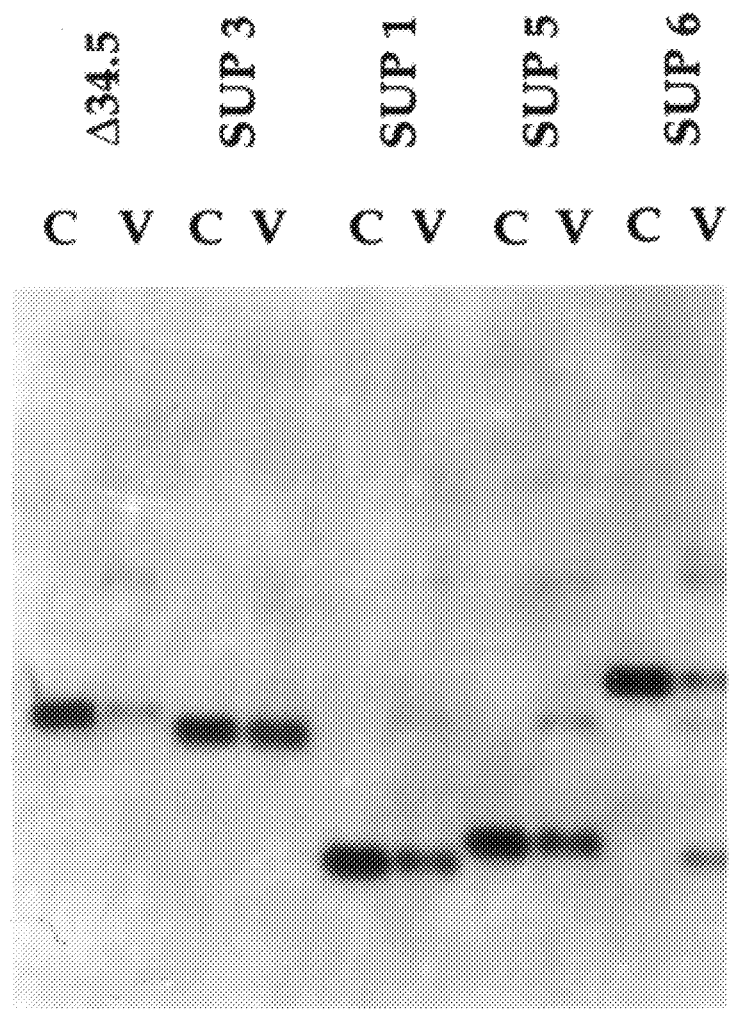
FIG. 10 is an autoradiograph of a Southern blot detailing the genetic structure of the BamHI Z fragment of the rescued suppressor isolates 1, 3, 5, and 6 (SUP1, SUP3, SUP5, and SUP6) and of the 34.5 deletion mutant SBg53e (Δ34.5). The lanes labelled with a "C" contained cloned plasmid DNA used in the marker rescue transfection which was subsequently digested with BamHI. The lanes labelled with a "V" contain BamHI digested viral DNA recovered after passage of the transfection lysate on U373 cells.

HSV-1 DNA from γ34.5 mutant viruses was transfected either alone or cotransfected with a specific rescue plasmid into permissive Vero cells. Each rescue plasmid contained the BstEII-NruI fragment from a specific suppressor isolate and could be recognized by its altered electrophoretic mobility relative to the wild type BamHI Z fragment specified in the parental HSV-1 γ34.5 mutant, as shown in FIG. 10 by comparing the Δ34.5 lane marked C with the C lanes of SUP1, SUP3, SUP5, and SUP6. Each transfection resulted in the appearance of approximately 90–200 plaques on permissive Vero cells. Cell-free lysates prepared from these transfections by freeze-thawing were then used to infect non-permissive U373 glioblastoma cells. At the first appearance of cytopathic effect, a freeze-thaw lysate was again prepared and used to infect a second set of U373 cells. At this juncture, the U373 cells which were infected with lysates derived from transfections of only 34.5 viral DNA appeared as uninfected monolayers. However, U373 cells infected with lysates derived from cotransfections of 34.5 viral DNA and each specific rescue plasmid all exhibited substantial cytopathic effect (data not shown). DNA was prepared from these rescued cultures to analyze the genotype of the resulting new viruses.

FIG. 10 presents a Southern analysis of BamHI Z region of the rescued isolates. In four separate instances, the rescued viruses had acquired the BamHI Z fragment specified by the suppressor plasmid present in the transfection as shown in FIG. 10 by a comparison of the C and V lanes of SUP1, SUP3, SUP5, and SUP6. Only the BstEII-NruI fragments in each of these plasmids differed from wild-type. In the case of SUP1 this minimal fragment was 109 base pairs. The additional bands hybridizing in the Δ34.5, SUP1, SUP5, and SUP6 lanes are due to variation in the repetitive component of the BamHI Z fragment. Similar alterations can be observed in the wild-type and SPBg5e lanes in FIG. 4. The slower mobility of the cloned SUP6 BamHI fragment in FIG. 10 is also due to variation in a reiterated component.

The Southern analysis shown in FIG. 10 demonstrated that the viruses which have acquired the suppressor phenotype, assessed by cytopathic effect on U373 cells, have acquired the genotype specified by the specific plasmid which was co-transfected with γ34.5 mutant HSV-1 DNA. Viruses harboring rearranged BamHI Z fragments had thus overtaken the entire population of γ34.5 mutant viruses in a single passage on non-permissive cells. This high frequency generation of the suppressor phenotype in a single pass contrasted to the multiple passes needed to select these isolates.

We claim:

1. A herpes simplex virus 1 (HSV-1) which is avirulent and selectively replicates in and destroys neoplastic cells having a genome from which the γ34.5 genes controlling virulence have been deleted and which has at least one additional mutation to the genome between the BstEII and NruI sites on the BamHI Z restriction fragment corresponding to nucleotides 145316 and 146008 (Genbank Accession No. X14112, strain 17).

2. A HSV-1 deposited under ATCC accession number VR-2510.

3. A pharmaceutical composition comprising the herpetic virus of claim 1 and a pharmaceutically acceptable carrier, adjuvant or diluent.

4. The pharmaceutical composition of claim 3, wherein the herpetic virus is an HSV-1 deposited under ATCC accession number VR-2510.

5. A vaccine comprising the herpetic virus of claim 1 and a pharmaceutically acceptable diluent, adjuvant or carrier.

6. The vaccine of claim 5, wherein the herpetic virus is an HSV-1 deposited under ATCC accession number VR-2510.

7. A method for immunizing a mammal against a herpetic virus comprising the step of inoculating the mammal with an immunity-inducing dose of the vaccine of claim 5 and a pharmaceutically acceptable diluent, adjuvant or carrier.

8. The method of claim 7, wherein the herpetic virus is an HSV-1 deposited under ATCC accession number VR-2510.

9. A herpes simplex virus 2 which is avirulent and selectively replicates in and destroys neoplastic cells having a genome from which the γ34.5genes controlling virulence have been deleted and which has at least one additional mutation to the genome between nucleotides 147500 and 148900 (Genbank Accession No. 286099, strain HG52).

10. A pharmaceutical composition comprising the herpetic virus of claim 9 and a pharmaceutically acceptable carriers adjuvant or diluent.

11. A vaccine comprising the herpetic virus of claim 9 and a pharmaceutically acceptable diluent, adjuvant or carrier.

12. A method for immunizing a mammal against a herpetic virus comprising the step of inoculating the mammal with an immunity-inducing dose of the vaccine of claim 11 and a pharmaceutically acceptable diluent, adjuvant or carrier.

* * * * *